United States Patent [19]

Suddath

[11] Patent Number: 5,438,884
[45] Date of Patent: Aug. 8, 1995

[54] FLUSH MOUNT FITTING FOR GAS EMISSION SAMPLE CONTAINER

[75] Inventor: James M. Suddath, West Bloomfield, Mich.

[73] Assignee: Bellaire Industries, Inc., Royal Oak, Mich.

[21] Appl. No.: 147,633

[22] Filed: Nov. 4, 1993

[51] Int. Cl.⁶ ............................................. G01N 1/14
[52] U.S. Cl. ............................... 73/864.62; 73/864.64; 73/864.63
[58] Field of Search ........... 73/864.62, 864.64, 864.63, 73/864.59

[56] References Cited

U.S. PATENT DOCUMENTS

| | | | |
|---|---|---|---|
| 4,546,659 | 10/1994 | Gill et al. | 73/864.62 |
| 4,893,731 | 1/1990 | Richter . | |
| 4,998,990 | 3/1991 | Richter et al. . | |
| 5,074,155 | 12/1991 | Vecere | 73/864.62 |
| 5,174,163 | 12/1992 | Gussman et al. | 73/864.62 |
| 5,218,874 | 6/1993 | Vecere . | |
| 5,239,877 | 9/1993 | Suddath et al. | 73/864.62 |

*Primary Examiner*—Richard E. Chilcot, Jr.
*Assistant Examiner*—Max Noori
*Attorney, Agent, or Firm*—Basile and Hanlon

[57] ABSTRACT

A gas emission sample container has a fitting mounted in an aperture formed in one side wall of an expansible body. The fitting includes a sleeve with a through bore and an enlarged diameter end collar. A ring member is mountable over the sleeve in surrounding engagement with the collar and traps the edges of the side wall of the container surrounding the aperture in the container therebetween. A lock nut threadingly mounted over the sleeve removably fixes the ring member over the collar with the exterior end of the collar being disposed substantially flush with the end of the ring member and the major portion of the side wall of the container. A coupler nut is connected to the sleeve for connecting the interior of the container and the fitting to a gas flow conduit. A seal is mounted about the sleeve between the collar and the ring member to form a seal between the edges of the side wall of the container surrounding the aperture in the container and the fitting.

10 Claims, 2 Drawing Sheets

FLUSH MOUNT FITTING FOR GAS EMISSION SAMPLE CONTAINER

BACKGROUND OF THE INVENTION

1. Field of the Invention

The present invention relates to gas emission sample containers for collecting gas emissions from motor vehicles and, more specifically, to fittings for use in gas emission sample containers.

2. State of the Art

Expandable, sealed containers or bags are employed for collecting and temporarily storing gas emissions from motor vehicles before the collected emissions are analyzed by suitable test equipment. Such containers are expandable to a predetermined volume to collect a known quantity of gaseous emissions.

Typically, a plurality of such containers, such as six containers, are connected through suitable conduits, valves, etc., to a test apparatus to collect separate quantities of gas emissions from a vehicle and from ambient atmosphere. The emission samples from a motor vehicle under test are collected in the sealed containers as the motor vehicle is operated according to a prescribed test schedule corresponding to various engine operating conditions.

The expandable containers include a fitting sealingly mounted in each container which is connected to the test apparatus to receive gas emissions from the vehicle under test. The fitting directs the gas emissions into the container for storage, as well as enabling the stored gas contents to be evacuated from the container for subsequent analysis. The fitting and the sealed container are made of a chemically inert material, such as a fluorinated carbon plastic, i.e., plastics sold under the registered trademarks TEFLON, KYNAR, and/or TEDLAR.

Accurate testing of gasses in a gas emission sample container requires the complete inflation of the container to a constant volume without internal dead spots as well as the complete evacuation of all gasses from the container. Specially designed, small, smooth fittings have been employed in gas emission sample containers to prevent the formation of internal dead spots during the evacuation of gas from such containers. In addition, hollow conduits or tubes having spaced apertures formed therein have been mounted within such containers and connected to the fitting to ensure complete and even inflation and evacuation of gas to and from the container, without stratification of the gas within the container.

However, previously devised fittings for gas emission sample containers have required a special design to minimize space within the container and to provide a smooth exterior shape to prevent the formation of dead spots during evacuation of gas from the container. As shown in U.S. Pat. No. 5,074,155, such fittings have also been designed with internal bores connected in fluid flow communication with a port extending through the fitting. Such designs have resulted in a high cost fitting due to their special construction and the requirement for a small, smooth shape.

Thus, it would be desirable to provide further improvements to fittings employed in gas emission sample containers. It would also be desirable to provide a fitting for a gas emission sample container which minimizes the volume consumed by the fitting within the interior of the gas emission sample container.

SUMMARY OF THE INVENTION

The present invention is a fitting for use in a gas emission sample container. The gas emission sample container includes a sealed, expandable body formed of a pair of side walls sealingly joined at their peripheral edges to form an expandable, hollow, interior cavity or chamber therein. An aperture is formed in one of the side walls and receives a fitting to establish a gas flow path between a motor vehicle or gas test equipment and the gas emission sample container.

In the present invention, the fitting includes a sleeve having an internal through bore and an enlarged diameter collar at one end. A ring member has a first end with a first aperture disposable over the sleeve. A side wall extends from the first end to a second end and form an internal bore disposable over the enlarged diameter collar at one end of the sleeve.

Means are provided for removably and fixedly mounting the ring member over the sleeve and collar on the sleeve such that the portion of the side wall of the container surrounding the aperture is disposed between the first end of the ring member and the collar on the sleeve and, further, the exterior end of the collar on the sleeve is flush with the second end of the side wall of the ring member. Seal means are mounted over the sleeve between the ring member and the collar for sealing the portion of the side walls of the container surrounding the aperture in the container. Finally, means are provided for coupling the through bore in the sleeve to an external gas flow path.

In one embodiment, the sleeve is externally threaded to threadingly receive a threaded lock nut which forms the fixing means to fixedly mount the ring member securely over the collar on the sleeve. The seal means may be mounted between the side wall of the container and the collar on the sleeve or between the side wall of the container and the ring member.

Further, radially extending grooves are formed in the exterior end of the collar to form gas flow paths when the gas emission sample container is nearly evacuated of gas.

The fitting for a gas emission sample container of the present invention overcomes certain deficiencies with previously devised fittings employed in gas emission sample containers. The present fitting is mounted in a gas emission sample container without any portion of the fitting extending into the interior of the container. This prevents the formation of dead spots in the container during evacuation of gas from the container. Further, the fitting is of simple construction for a low manufacturing cost and ease of use.

BRIEF DESCRIPTION OF THE DRAWINGS

The various features, advantages, and other uses of the present invention will become more apparent by referring to the following detailed description and drawing in which.

DESCRIPTION OF THE PREFERRED EMBODIMENTS

Figure 1:
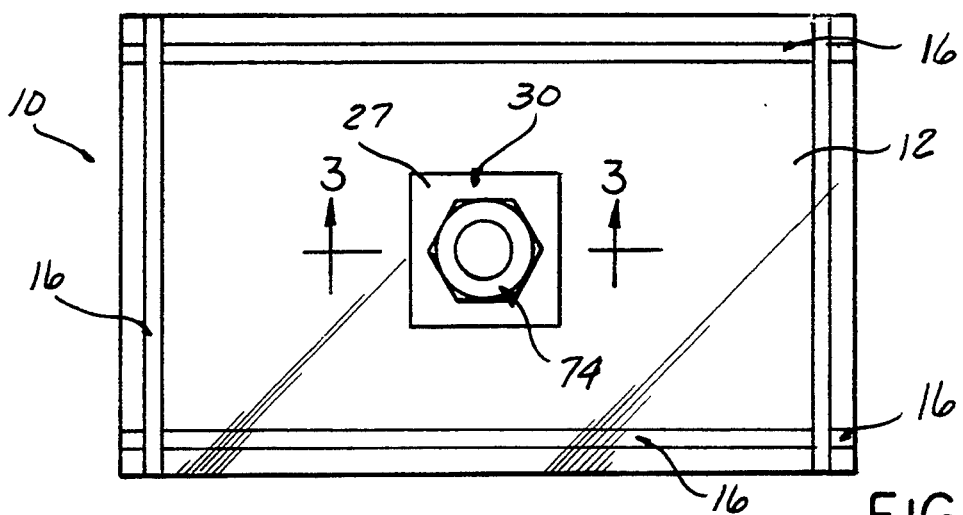
FIG. 1 is a plan view of a gas emission sample container having a fitting constructed in accordance with the teachings of the present invention mounted therein.
Figure 2:
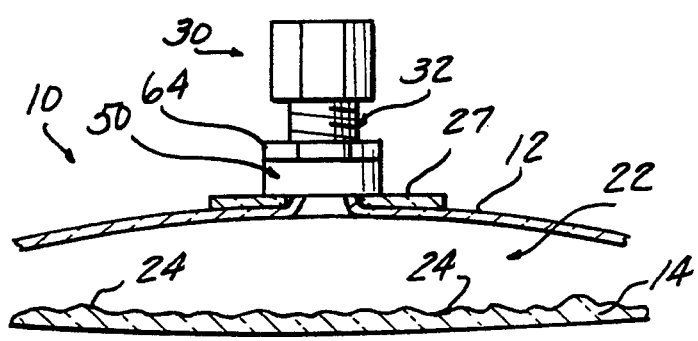
FIG. 2 is a partial, longitudinal cross sectional view through the container shown in FIG. 1.
Figure 3:
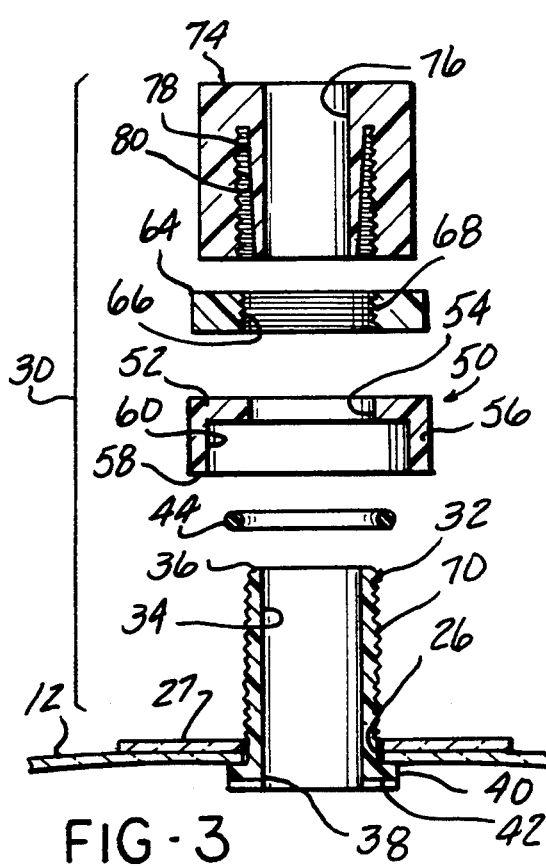
FIG. 3 is an exploded, cross sectional view generally taken along line 3—3 in FIG. 1.

Referring now to the drawing, and to FIGS. 1-3 in particular, there is illustrated a gas emission sample container 10 which is connectible to a motor vehicle, for example, to collect and temporarily store gas emissions therefrom. The container 10 is also connectible to suitable test equipment, not shown, to supply such stored gas emissions to the test equipment for subsequent testing and/or analysis. As shown in FIGS. 1 and 2, the gas emission sample container 10 comprises a sealed enclosure of any shape, such as rectangular, square, circular, etc. It will be understood that a rectangular shape for the container 10 is illustrated by way of example only. Further, the container 10 may be provided in different sizes depending upon the requirements of a particular test application.

The sealed container or bag 10 is formed of two flexible sheets of chemically inert material. Preferably, fluorinated plastics chosen from the fluorocarbon family, such as those sold under the trademarks TEFLON, TEDLAR and HALON, may be employed. As shown in FIG. 2, the sealed container 10 is formed of a first or front sheet 12 and a second or back sheet 14, each of a single thickness or ply. Typically, the single ply sheets 12 and 14 are 2 or 4 mils. in thickness. Front and back sheet arrangements of two or more plys each are also possible. The front and back sheets 12 and 14, respectively, are sealingly connected at their peripheral edges by any suitable means, such as by heat seams 16. Such a sealing method forms a recess on one side of the joined sheets 12 and 14 and a small projection or bump on the opposite surface. For additional sealing capability, two spaced heat seams 16 may be employed about the peripheral edges of the front and back sheets 12 and 14. The seam or seams 16 seal the peripheral edges of the front and back sheets 12 and 14 and form a hollow, expandable, internal cavity 22, shown in FIG. 2, within the interior of the sealed container 10.

Optionally, at least one of the sheets, such as the second sheet 14 of the container 10, includes a plurality of spaced, discrete projections 24, as shown in FIG. 2. The projections 24 extend outward from one surface of the sheet 14 toward the opposed sheet 12 and are disposed in the interior cavity 22 of the sealed container 10. The projections 24 may have irregular shapes and may be disposed at irregular spacings as shown in FIG. 2. However, the projections 24 are preferably formed on substantially the entire surface of the sheet 12.

The projections 24 are formed in the sheet 14 by any suitable means, such as the use of rolls or a press which permanently deforms the sheet 14 into the desired projection shape and location. As shown in FIG. 2, the projections 24 generally taper from the surface of the sheet 14 to an apex. It will be understood that projections 24 having any other shape may also be employed to practice the present invention. Further details concerning the shape and construction of the projections 24 may be had by referring to pending and allowed U.S. patent application, Ser. No. 07/905,900, the contents of which are incorporated herein by reference.

A plurality of gas flow paths are formed between the spaced, adjacent projections 24. The gas flow paths extend over substantially the entire surface of the sheet 14 and remain even when the container 10 is evacuated and the opposed sheet 12 is drawn into close proximity or contact with the sheet 14. The gas flow paths thus insure a complete filling of the container 10 when gas is introduced into the interior cavity 22 of the container 10 through a fitting 30 as well as a complete evacuation of the entire volume of gas from the container 10 through the fitting 30.

Figure 4:
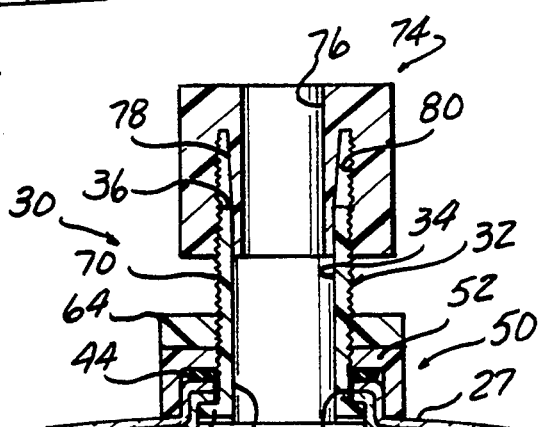
FIG. 4 is a cross sectional view, similar to FIG. 3, but showing the position of the components of the fitting of the present invention in their completely engaged, mounting state.

An aperture 26, shown in FIGS. 3 and 4 is formed in one of the side walls, such as side wall 12, of the container 10 and opens to the interior cavity 22 within the container 10. Optionally, a thin reinforcing member, such as a reinforcing strip or tape 27, is adhesively mounted on the side wall 12 of the container 10 surrounding the aperture 26 in the sheet 12. A corresponding aperture is formed in the reinforcing strip 27 in alignment with the aperture 26 in the sheet 12 of the container 10.

The fitting 30, shown in FIGS. 1-5, is mounted on the container 10 for controlling the flow of gas to and from the interior cavity 22 in the container 10. The fitting 30 includes components formed of a chemically inert material. Any suitable material, such as a fluorocarbon or fluorinated plastic may be employed. By way of example, fluorocarbons sold under the trademark TEFLON and those sold under trade or chemical names of TFE, PTFE, FEP, PFA and ECTFE, may be employed. Other fluorocarbonated plastics sold under the trademarks FLOUNS, HALARS and KYNAR may be employed. Additionally, polyvinylfluorines, sold under the trademark TEDLAR or trade names, PVF and PV2F, may also be employed.

As shown in detail in FIGS. 3 and 4, the fitting 30 includes a tubular sleeve 32 having a through bore 34 extending therethrough from a first end 36 to a second end 38. An enlarged diameter collar 40 is formed at the second end 38 of the sleeve 32 and has a diameter larger than the diameter of the tubular portion of the sleeve 32 to form an annular, enlarged surface at the second end 38 of the sleeve 32.

Figure 5:
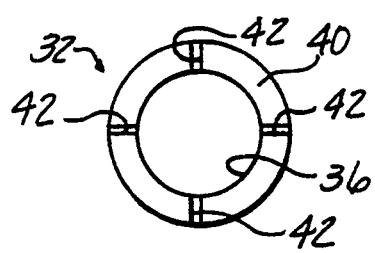
FIG. 5 is a bottom view of the sleeve employed in the fitting shown in FIGS. 1-4.

As shown in FIG. 5, in at least one, and preferably a plurality of radially extending grooves or slots 42 are formed in the exterior surface of the collar 40 adjacent the second end 38 of the sleeve 32. The grooves 42 extend radially outward from the bore 36 in the sleeve 32 and form gas flow paths opening to the bore 36 in the sleeve 32 which assist in preventing the formation of dead spots within the interior chamber 22 of the container 10 when the container 10 is substantially evacuated of gas.

Figure 6:
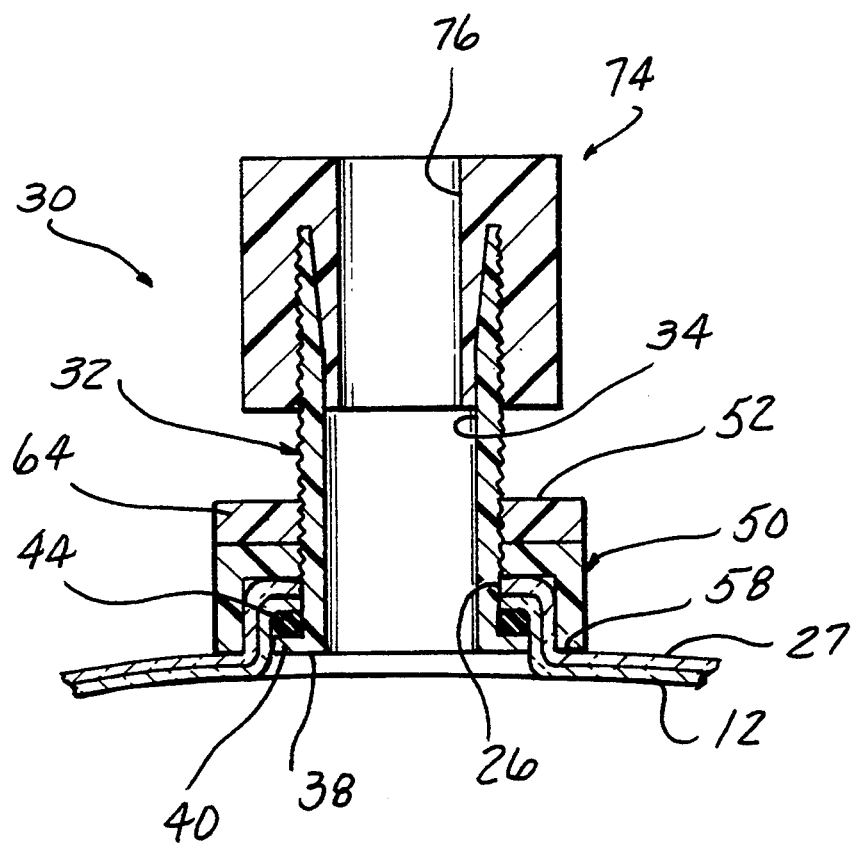
FIG. 6 is a cross-sectional view similar to FIG. 4; but showing an alternate mounting position of the seal.

A seal means 44 is mounted about the sleeve 32 for sealing the sleeve 32 to the reinforcing strip 27 and the sheet 12 of the container 10. The seal means 44, which may be, by way of example, an O-ring, is mounted in contact with the collar 40 on the sleeve 32 below the sheet 12 or, as shown in FIG. 4, on the portion of the reinforcing strip 27 and the sheet 12, as shown in FIG. 6, disposed on top of the collar 40 of the sleeve 32.

A compression ring member 50 has a generally annular shape with a first end 52 having an aperture 54 formed therein. The aperture 54 is alignable with the bore 34 in the sleeve 32 to form a gas flow path therethrough. The compression ring member 50 has an annular side wall 56 which extends from the first end 52 to a second end 58 of the ring member 50. The interior portion of the ring member 50 within the annular side wall 58 is hollow, as shown in FIG. 3 and forms an interior bore 60 which is adapted to fit over the enlarged collar 40 of the sleeve 32, as shown in FIG. 4.

Means are provided for removably and fixedly mounting the ring member 50 over the sleeve 32 such that side wall 12 of the container 10 bounding the aperture 26 in the side walls 12 is drawn up and disposed between the first end 52 of the ring member 50 and the collar 40 on the sleeve 32. In this configuration, the exterior, second end 38 of the sleeve 32 is drawn up into substantial flush alignment with the major portion of the surface of the sheet 12 such that no portion of the fitting 30 extends into the interior chamber 22 of the container 10.

Preferably, the means for mounting the ring member 50 over the sleeve 32 comprises a lock nut 64 having an internal bore 66 with a plurality of internal threads 68 formed therein. The bore 66 is alignable with the aperture 54 in the first end 52 of the ring member 50. Further, the internal threads 68 on the lock nut 64 are threadingly engagable with external threads 70 formed along the tubular portion of the sleeve 32. The threading engagement of the lock nut 64 on the sleeve 32 holds the ring member 50 in a compressed state about the collar 40 on the sleeve 32 and causes the portions of the sheet 12 and the reinforcing strip 27 bounding the aperture 26 in the sheet 12 to be drawn up, as shown in FIG. 4, out of the general plane of the major portion of the surface of the sheet 12 between the collar 40 on the sleeve 32, the seal means 44 and the first end 52 of the ring member 50. Such threading engagement also compresses the seal means 44 to form a complete seal between the sleeve 32 and the aperture 26 in the sheet 12 of the container 10.

Alternately, the mounting means may be formed by internal threads in the first end of the ring member 50 which engage the threads on the tubular portion of the sleeve 32.

Means are also provided for coupling the fitting 30 to a gas conduit for supplying gas to the chamber 22 in the container 10 from a motor vehicle undergoing testing as well as to provide a gas flow path from the chamber 22 in the container 10 to suitable gas test equipment, not shown, for analyzing the constituents of the gas.

The coupling means preferably comprises a coupler nut 74, such as that disclosed in U.S. Pat. No. 3,977,708 and manufactured by Fluoroware, Inc. The contents of this patent are incorporated herein by reference with respect to the construction of the coupler nut 74.

As is generally disclosed therein, the coupler nut 74 includes a central through bore 76 which is alignable with and forms a continuous gas flow path with the bore 34 in the sleeve 32 for the flow of gas emissions to and from the interior chamber 22 in the container 10. A second outer bore 78 is formed in the nut 74 between the central bore 76 and the exterior side walls of the coupler nut 74. Internal threads 80 are formed in the bore 78 and threadingly engage the threads 70 on the sleeve 32 to releasably connect the coupler nut 74 to the sleeve 32 of the fitting 30.

The coupler nut 74 may have the generally straight configuration shown in FIGS. 3 and 4 or, optionally, it may be provided as a 90° elbow. A gas flow conduit, not shown, is releasably mountable in the bore 76 and the coupler nut 74 to connect the fitting 30 and the interior chamber 22 in the container 10 to a motor vehicle undergoing test or to gas emission test equipment.

In assembling the fitting 30 on the container 10, the enlarged collar 40 of the sleeve 32 is initially inserted through the aperture 26 in the sheet 12 into the interior chamber 22 in the container 10. The seal means or O-ring 44 may be initially disposed on the shoulder of the sleeve 32 between the tubular portion of the sleeve 32 and the collar 40 or it may be mounted over the sheet 12, as shown in FIG. 4, after the sleeve 32 has been mounted through the aperture 26 in the sheet 12 of the container 10. The compression ring member 50 is then mounted over the sleeve 32 until the second end 58 thereof contacts the reinforcing strip 27 on the sheet 12 of the container 10. The lock nut 64 is threaded over the sleeve 32 into tight engagement with the sleeve 32 to force the ring member 50 over the exterior peripheral edge of the collar 40 on the sleeve 32 and to bring the peripheral edge portions of the sheet 12 and the reinforcing strip 27 surrounding the aperture 26 in the sheet 12 out of the plane of the surface of the sheet 12 to trap such peripheral edge portions between the seal 44 and the collar 40 of the sleeve 32. In this position, as shown in FIG. 4, the second end 38 of the sleeve 32 is substantially flush with the general plane of the sheet 12 such that no portion of the fitting 30 extends into the interior chamber 22 of the container 10. The coupler nut 74 is then threaded onto the sleeve 32 and the gas flow conduit, not shown, connected thereto to establish a gas flow path between the container 10 and either a motor vehicle undergoing test or gas emission test equipment.

In summary, there has been disclosed a unique fitting for a gas emission sample container which provides gas flow communication between the interior chamber in the gas emission sample container and either a motor vehicle undergoing test or gas emission test equipment. The unique fitting is mountable in the container in a sealed arrangement; but with no portion of the fitting extending into the interior chamber of the container 10. This prevents the formation of dead spots within the container 10 during the evacuation of gas from the container 10 to enable more accurate gas emission test results to be obtained. The fitting of the present invention is simple in construction for a low manufacturing cost and ease of use.

What is claimed is:

1. A gas emission sample apparatus for receiving and storing gas emissions from test apparatus, the apparatus comprising:

a container formed of a sealed expansible member having side walls, with an aperture formed in and surrounded by portions of one of the side walls;

a sleeve having first and second ends and a through bore extending between the first and second ends, an enlarged diameter collar formed at the second end of the sleeve;

a ring member having a first end with a first aperture formed therein disposable over the sleeve and a side wall extending from the first end to a second end and forming a hollow bore in the ring member disposable over the collar of the sleeve;

means for removably and fixedly mounting the ring member over the sleeve and the collar such that the portions of the side wall of the container surrounding the aperture in the container are disposed between the first end of the ring member and the collar on the sleeve and an exterior end of the collar is substantially flush with the second end of the ring member and a major portion of the one of the side walls of the container;

seal means, mountable over the sleeve and between the ring member and the collar, for sealing the aperture in the container; and means for coupling the through bore in the sleeve to an external gas flow path.

2. The apparatus of claim 1 wherein the seal means is disposed about the sleeve in engagement with the collar on the sleeve and the portions of the side wall of the container surrounding the aperture in the side wall of the container.

3. The apparatus of claim 1 wherein the seal means is disposed between the first end of the ring member and the portions of the side wall of the container surrounding the aperture in the one side wall of the container.

4. The apparatus of claim 1 wherein the mounting means comprises:

a lock nut threadingly engageable with the sleeve for fixedly mounting the ring member in surrounding engagement with the collar on the sleeve.

5. The apparatus of claim 1 wherein the mounting means comprises:

external threads formed on the sleeve; and a lock nut having internal threads engageable with the external threads on the sleeve.

6. The apparatus of claim 1 wherein the bore in the ring member has a length substantially equal to the axial length of the collar on the sleeve.

7. The apparatus of claim 1 wherein a diameter of the bore in the ring member is slightly larger than a diameter of the collar on the sleeve.

8. The apparatus of claim 1 wherein a plurality of radially extending grooves are formed on the exterior end of the collar on the sleeve.

9. The apparatus of claim 1 wherein: the seal means comprises an O-Ring.

10. A gas emission sample apparatus for receiving and storing gas emissions, the apparatus comprising:

a container formed of a sealed expansible member having side walls, with an aperture formed in and surrounded by portions of one of the side walls;

a sleeve having first and second ends and a through bore extending between the first and second ends, an enlarged diameter collar formed at the second end of the sleeve;

the collar having a first surface forming a shoulder at a juncture with the sleeve, a second opposed surface forming the second end of the sleeve, and a peripheral edge between the first and second surfaces;

a ring member having a first end with a first aperture formed therein disposable over the sleeve and a side wall extending from the first end to a second end and forming a hollow bore in the ring member disposable over the collar of the sleeve;

means for removably and fixedly mounting the ring member over the sleeve and the collar;

seal means, mountable over the sleeve and between the ring member and the collar, for sealing the aperture in the container;

the mounting means mounting the ring member encompassingly about the peripheral edge of the collar such that the portions of the one of the side walls of the container surrounding the aperture in the container are disposed between the first end of the ring member and the collar, and the second surface of the collar is substantially flush with the second end of the ring member and the one of side walls of the container; and means for coupling the through bore in the sleeve to an external gas flow path.

* * * * *